United States Patent [19]

Matsui et al.

[11] 4,391,907
[45] Jul. 5, 1983

[54] METHOD FOR PRODUCING L-VALINE BY FERMENTATION

[75] Inventors: Hiroshi Matsui; Takayasu Tsuchida, both of Kawasaki; Shigeru Nakamori, Yokohama, all of Japan

[73] Assignee: Ajinomoto Company Incorporated, Tokyo, Japan

[21] Appl. No.: 212,123

[22] Filed: Dec. 2, 1980

[30] Foreign Application Priority Data

Dec. 13, 1979 [JP] Japan .................................. 54-161974

[51] Int. Cl.$^3$ ....................... C12N 1/20; C12N 15/00; C12P 13/08; C12R 1/185; C12R 1/19
[52] U.S. Cl. .................................... 435/115; 435/172; 435/253; 435/848; 435/849
[58] Field of Search ............... 435/115, 172, 317, 848, 435/849, 253

[56] References Cited

U.S. PATENT DOCUMENTS

| | | | |
|---|---|---|---|
| 2,975,105 | 3/1961 | Huang | 435/849 X |
| 3,893,888 | 7/1975 | Tsuchida et al. | 435/115 |
| 4,237,224 | 12/1980 | Cohen et al. | 435/849 X |
| 4,278,765 | 7/1981 | Debabov et al. | 435/115 X |

*Primary Examiner*—Esther M. Kepplinger
*Attorney, Agent, or Firm*—Oblon, Fisher, Spivak, McClelland & Maier

[57] ABSTRACT

An L-valine-producing microorganism which is constructed by incorporation into a host strain of the genus Escherichia of a hybrid plasmid having inserted therein a DNA fragment with genetic information related to L-valine production which is derived from a donor strain of the genus Escherichia which is resistant to a valine analogue, is useful for the production of high levels of L-valine by fermentation.

11 Claims, No Drawings

METHOD FOR PRODUCING L-VALINE BY FERMENTATION

BACKGROUND OF THE INVENTION

1. Field of the Invention

The present invention relates to a method for producing L-valine by fermentation, and particularly relates to a method for producing L-valine with a microorganism constructed by a gene recombination technique.

2. Description of the Prior Art

Although a wild strain of *Escherichia coli* produced in the presence of a specific surfactant 1.42 g/dl L-valine (Japanese Published Examined Patent Application No. 21752/1966), most of wild strains do not produce L-valine in the medium. In order to render a wild strain capable of producing L-valine from carbohydrates, it has been necessary to induce artificial mutants from the wild strain. There are many known valine-producing artificial mutants. Most of the known valine-producing mutants are resistant to 2-thiazolealanine, and belong to the genus Brevibacterium or Corynebacterium.

Known valine high producers are *Brevibacterium lactofermentum* FERM-P 1963, which is resistant to 2-thiazole-alanine and requires for growth L-isoleucine (Japanese Published Examined Patent Application No. 116/1977) and which produced 2.51 g/dl L-valine, and *Brevibacterium lactofermentum*, KY 10614, which is resistant to S-2-aminoethyl-L-cysteine and which produced 3.05 g/dl L-valine.

It has however, become difficult to increase the yields of L-valine using the artificial mutation techniques. A need therefore, continues to exist for the development of novel methods for producing L-valine in high yields.

SUMMARY OF THE INVENTION

It is therefore an object of the invention to provide a method for producing L-valine in high yields.

These and other objects of the invention, which will hereinafter become more readily apparent, have been attained by providing:

Culturing in a culture medium an L-valine-producing microorganism which is obtained by incorporating into a recipient strain of the genus Escherichia, a hybrid plasmid having inserted therein a DNA fragment with genetic information controlling L-valine production which is derived from a donor strain of the genus Escherichia which is resistant to an L-valine analogue and recovering the L-valine accumulated in the culture medium.

DETAILED DESCRIPTION OF THE PREFERRED EMBODIMENTS

The inventors have succeeded in providing a method for producing L-valine by fermentation, which comprises: culturing in a culture medium an L-valine-producing microorganism constructed by incorporating a hybrid plasmid in a recipient of the genus Escherichia and recovering the L-valine accumulated in the culture medium, said hybrid plasmid containing a DNA fragment possessing genetic information related to L-valine production and obtained from a microorganism of the genus Escherichia resistant to a valine-analogue.

The DNA-donor strain used to construct the L-valine producer of this invention is a microorganism of the genus Escherichia possessing genetic information related to L-valine production. Strains having higher productivity of L-valine are used preferably as the DNA-donor. The mutant resistant to the valine-analogue used as the DNA-donor can be obtained by conventional mutation techniques.

The valine-analogues are those which inhibit the growth of Escherichia strains, but the inhibition is suppressed partially or completely when L-valine coexists in the medium. Examples of valine-analogues are $\beta$-hydroxy-leucine, $\beta$-2-thienyl-alanine, 1,2,4-triazole-alanine, 2-thiazole-alanine, $\alpha$-amino-butyric acid, $\beta$-hydroxy-valine, norvaline, $\alpha$-amino-isobutane-sulfonic acid, methallyl-glycine, and $\omega$-dehydro-alloisoleucine.

Chromosomal DNA is extracted from the DNA donor in a well known manner and treated with a restriction endonuclease by a well known method (Biochem. Biophys. Acta 383: 457 (1975)).

The plasmid or phage DNA used as the vector in the synthesis procedure is also treated with a restriction endonuclease in an analogous manner. Various kinds of restriction endonucleases can be used, if the digestion of the chromosomal DNA is done partially. Thereafter, the digested chromosomal and vector DNAS are subjected to a ligation reaction.

Recombination of DNA to prepare the recombinant plasmid can be carried out by incorporating with terminal transferase, deoxyadenylic acid and thymidylic acid, or deoxyguanylic acid and deoxycytidylic acid into the chromosomal DNA fragment and cleaved vector DNA, and by subjecting the modified chromosomal DNA fragment and the cleaved vector DNA to an annealing reaction.

As a suitable vector DNA, a conventional vector can be employed such as Col El, pSC 101, pBR 322, pACYC 177, pCR 1, R6K, or $\lambda$-phage, or their derivatives.

The hybrid DNA thus obtained can be incorporated into a microorganism of the genus Escherichia by conventional transformation techniques, J. Bacteriol., 119: 1072 (1974). The desired transformant is screened using a medium on which only a clone, having one or both of the characteristics of L-valine productivity possessed by the chromosomal DNA fragment and those possessed by vector DNA, can grow.

As the recipient microorganism for the hybrid DNA, an L-valine-auxotroph is usually used, since it is conventional to distinguish the valine-producing transformant from the recipient. Desirably, a mutant already having higher productivity of L-valine is used as the recipient, to obtain better results.

The methods of culturing the L-valine-producing strains thus obtained are conventional, and are similar to the methods for the cultivation of known L-valine-producing microorganisms. Thus, the culture medium employed is a conventional one containing carbon sources, nitrogen sources, inorganic ions and, when required, minor organic nutrients such as vitamins or amino acids. Examples of suitable carbon sources include glucose, sucrose, lactose, starch hydrolysate and molasses. Gaseous ammonia, aqueous ammonia and ammonium salts and other nitrogen containing materials can be used as the nitrogen source.

Cultivation of the recombinant microorganisms is conducted under aerobic conditions in which the pH and the temperature of the medium are adjusted to a suitable level and continued until the formation of L-valine ceases.

The L-valine accumulated in the culture medium can be recovered by conventional procedures.

By the method of the present invention, L-valine can be produced in higher yields than has been achieved in previously known methods using artificial mutants of Escherichia.

Having generally described this invention, a further understanding can be obtained by reference to certain specific examples which are provided herein for purposes of illustration only and are not intended to be limiting unless otherwise specified.

EXAMPLE 1

(1) Preparation of chromosomal DNA possessing genetic information related to L-valine production

*Escherichia coli* AJ 11470 (FERM-P 5211, NRRL B-12285), a mutant resistant to β-hydroxyleucine, and derived from K-12 (ATCC 10798) by exposing K-12 cells to 250 µg/ml of N-methyl-N'-nitro-N-nitrosoguanidine in a citric acid buffer of pH 5.5 at 0° C. for 60 minutes, and separating the colony which appeared on the agar medium, was cultured at 37° C. for 3 hours with shaking in 1 l of L-medium containing 1 g/dl peptone, 0.5 g/dl yeast extract, 0.1 g/dl glucose and 0.5 g/dl NaCl (pH was adjusted to 7.2), and bacterial cells in the exponential growth phase were harvested. Chromosomal DNA was extracted by a conventional phenol-method, and 2.8 mg of purified DNA was obtained.

(2) Preparation of vector DNA

As the vector, DNA of pBR 322 was prepared as follows:

A strain of *Escherichia coli* K-12 harboring the plasmid pBR 322 was incubated at 37° C. in 1 l of a glucose-"casamino acid"-inorganic salts medium containing: 2 g glucose, 1 g NH$_4$Cl, 3 g Na$_2$HPO$_4$, 5 g NaCl, 0.1 g MgSO$_4$.7H$_2$O, 0.015 g CaCl$_2$.2H$_2$O, 20 g "casamino acid" (casein hydrolysate), 0.05 g thymine, 0.05 g L-tryptophan and 100 µg thiamine HCl per liter (pH was adjusted to 7.2). After the strain was incubated until the late log phase, 170 µg/ml of chloramphenicol was added to the culture medium. Through this process, the plasmid DNA was amplified and accumulated abundantly in the bacterial cells.

After 16 hours of the incubation, cells were harvested and then lysed by treatment with lysozyme and sodium dodecylsulfate. The lysate was centrifuged at 30,000 xg for 1 hour to obtain the supernatant. After concentrating the supernatant, 550 µg of the plasmid DNA was obtained by fractionation using cesium chloride ethidium bromide equlibrium density gradient centrifugation.

(3) Insertion of chromosomal DNA fragment into vector

Ten µg of the chromosomal DNA was treated with the restriction endonuclease EcoRI, Pst I, Hind III, Sal I or Bam HI at 37° C. for 5, 10, 20, 30 and 60 minutes, respectively, to cleave the DNA chains, and then heated at 65° C. for 5 minutes, respectively. Ten µg of the vector DNA was also treated with each of the restriction endonucleases mentioned above at 37° C. for 1 hour to cleave the DNA completely, and then heated at 65° C. for 5 minutes.

The digested chromosomal DNA solution and cleaved vector DNA solution were mixed and subjected to the ligation reaction of DNA fragments by a T$_4$ phage DNA-ligase in the presence of ATP and dithiothreitol at 10° C. for 24 hours. The reaction mixture was then heated at 65° C. for 5 minutes, and two folds volume of ethanol was added to it. The precipitated recombinant DNA was recovered.

(4) Genetic transformation with the hybrid plasmid harboring the genetic information related to L-valine production A valine and isoleucine requiring strain, *Escherichia coli* ilv-5, NRRL B-12284, which was derived from *Escherichia coli* K-12 N-methyl-N'-nitro-N-nitrosoguanidine mutagenesis in by 250 g/ml a citric acid buffer of pH 5.5 at 0° C. for 60 minutes, was cultured in 10 ml of L-medium at 37° C. with shaking. Cells in exponential growth phase were harvested, and suspended in 0.1 M MgCl$_2$ solution and then in 0.1 M CaCl$_2$ solution in an ice-bath, whereby "competent" cells having the ability of DNA uptake were prepared.

Into the competent cell suspension, the DNA obtained in step (3), which contains the hybrid plasmid DNA, was added. The suspension was kept in an ice-bath for 30 minutes, then heated at 42° C. for 2 minutes, and again allowed to stand in an ice-bath for 30 minutes, the cells, thus being incorporated with the hybrid plasmid DNA, were inoculated into L-medium and the medium was shaken at 37° C. for 4 hours, whereby the transformation reaction was completed. The cells were harvested, washed, and resuspended. A small portion of the cell suspension was spread on an agar plate containing, 5 g glucose, 1 g (NH$_4$)$_2$SO$_4$, 7 g K$_2$HPO$_4$, 2 g KH$_2$PO$_4$, 0.4 g MgSO$_4$.7H$_2$O, 0.5 sodium citrate.2H$_2$O, and 20 g agar, per liter, (pH was adjusted to 7.2). The plate was incubated at 37° C. for 3 days.

Colonies appeared on the plate were picked up, and strains resistant both to ampicillin (50 µg/ml) and tetracycline (5 µg/ml) were selected using agar-L-medium, and among them a valine-producing transformant was separated by the formation of halo on a mini mum-agar-medium on which containing 100 µg/l L-isoleucine valine and isoleucine-requiring mutant No. ilv-5 had previously been spread.

Thus, AJ 11501, FERM-P 5306, NRRL B-12287 was obtained as the valine-producing transformant.

(5) Production of L-valine by the novel L-valine-producing strain

Table 1 shows the experimental result of the fermentative production of L-valine using the strains NRRL B-12287 and the DNA-donor strain AJ 11470.

The fermentation medium contained 5 g/dl glucose, 2.5 g/dl ammonium sulfate, 0.2 g KH$_2$PO$_4$, 0.1 g/dl MgSO$_4$.7H$_2$O, 0.05 g/dl yeast extract, 100 µg/dl thiamine.HCl, 1 mg/dl FeSO$_4$.7H$_2$O, 1 mg/dl MnSO$_4$.4H$_2$O and 2.5 g/dl CaCo$_3$ (separately sterilized) and the pH was adjusted to 7.2.

Twenty ml batches of the fermentation medium were placed in 500 ml flasks, inoculated with one loopful inoculum of the test microorganism, and the cultivation was carried out at 31° C. for 72 hours.

The amount of L-valine in the supernatant of the fermentation broth was determined by microbiological assay.

TABLE 1

| Microorganism tested | L-valine produced (mg/dl) |
|---|---|
| AJ 11470 | 30 |
| NRRL B-12287 | 80 |

EXAMPLE 2

(1) Preparation of the hybrid plasmid harboring the genetic information related to L-valine production The transformant AJ 11501 (NRRL B-12287) was cultured in 1 l of L-medium at 37° C. for 5 hours with shaking. Cells in exponential growth phase were harvested and then lysed by treatment with a lysozyme and SDS. The lysate was centrifuged at 30,000 xg for 1 hour to obtain the supernatant, the supernatant was concentrated, and 310 μg of the hybrid plasmid DNA was obtained by fractionation using cesium chloride-ethidium bromide equilibrium density gradient centrifugation.

(2) Genetic transformation with the hybrid plasmid harboring the genetic information related to L-valine production AJ 11470 was inoculated in 10 ml of L-medium and cultured at 37° C. with shaking. Cells in exponential growth phase were harvested, and suspended in 0.1 M $MgCl_2$ solution and then in 0.1 M $CaCl_2$ solution in an ice-bath, obtaining competent cells. The competent cells suspension was added with the hybrid plasmid DNA obtained in step (1), and the suspension was kept in an ice-bath for 30 minutes, then heated at 42° C. for 2 minutes, and again allowed to stand in an ice-bath for 30 minutes. The cells obtained were inoculated in L-medium, and cultured at 37° C. for 4 hours with shaking. The cultured liquid was spread on an L-agar-medium containing ampicillin (50 μg/ml) and tetracycline (5 μg/ml). After 4 hours incubation at 37° C., colonies appeared on the L-agar-medium were picked up. Valine-producing transformants were selected by the formation of halo on a minimum-agar-medium containing 100 mg/l L-isoleucine on which a valine and isoleucine-requiring mutant, No. ilv-5 had previously been spread.

Thus, transformants resistant both to ampicillin and tetracycline and capable of producing L-valine were separated and purified, and the highest valine-producer AJ 11502, FERM-P 5307, NRRL B-12288) was obtained.

(3) Production of L-valine by the novel L-valine-producing strain

L-valine productivity of NRRL B-12288 was tested by the manner shown in Example 1. AJ 11470 was cultured also for comparison.

The results are shown in Table 2.

TABLE 2

| Tested strains | L-valine produced (mg/dl) |
|---|---|
| *Escherichia coli* AJ 11470 | 30 |
| *Escherichia coli* NRRL B-12288 | 150 |

What is claimed is:

1. A method of producing L-valine by fermentation which comprises culturing in a culture medium an L-valine-producing microorganism selected from the group consisting of *Escherichia coli* NRRL B-12287 and *Escherichia coli* NRRL B-12288 which is obtained by incorporation into a recipient strain of the genus Escherichia, of a hybrid plasmid having inserted therein a DNA fragment with genetic information related to L-valine production which fragment is derived from a donor strain of the genus Escherichia which is resistant to a valine analogue, and recovering the L-valine accumulated in the culture medium.

2. The method of claim 1, wherein said recipient strain is resistant to β-hydroxy-leucine.

3. The method of claim 1, wherein said recipient strain belongs to *Escherichia coli*.

4. The method of claim 1, wherein said donor strain belongs to *Escherichia coli*.

5. The method of claim 1, wherein said recipient strain is *Escherichia coli* K-12 or a mutant thereof.

6. The method of claim 1, wherein said donor strain is *Escherichia coli* K-12 or a mutant thereof.

7. The method of claim 1, wherein said hybrid plasmid is derived from pBR 322.

8. The method of claim 5, wherein said L-valine producing microorganism is NRRL B-12287.

9. The method of claim 5, wherein said L-valine producing microorganism is NRRL B-12288.

10. A biologically pure culture of the microorganism Escherichia, having the identifying characteristics of NRRL B-12287, said culture being capable of producing L-valine in recoverable quantity upon fermentation in an aqueous medium containing assimilable nutrients.

11. A biologically pure culture of the microorganism Escherichia, having the identifying characteristics of NRRL B-12288, said culture being capable of producing L-valine in recoverable quantity upon fermentation in an aqueous medium containing assimilable nutrients.

* * * * *